(12) United States Patent
Frey et al.

(10) Patent No.: US 6,626,896 B2
(45) Date of Patent: *Sep. 30, 2003

(54) METHOD OF CORRECTING VISION

(75) Inventors: Rudolph W. Frey, Orlando, FL (US); James H. Burkhalter, Orlando, FL (US); Gary P. Gray, Orlando, FL (US); Neil Zepkin, Casselberry, FL (US); George Richard Downes, Jr., Orlando, FL (US); John E. McWhirter, Orlando, FL (US)

(73) Assignee: Alcon, Inc., Hunenberg (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 94 days.

This patent is subject to a terminal disclaimer.

(21) Appl. No.: 09/742,884

(22) Filed: Dec. 21, 2000

(65) Prior Publication Data

US 2001/0016737 A1 Aug. 23, 2001

Related U.S. Application Data

(63) Continuation of application No. 09/376,133, filed on Aug. 17, 1999, which is a continuation of application No. 08/232,615, filed on Apr. 25, 1994, now Pat. No. 5,980,513.

(51) Int. Cl.⁷ ................................................. A61F 9/007

(52) U.S. Cl. ............................... 606/12; 606/5; 606/10; 606/13

(58) Field of Search ............................. 606/2–6, 10–14

(56) References Cited

U.S. PATENT DOCUMENTS

| 3,712,716 | A | 1/1973 | Cornsweet et al. |
| 3,880,501 | A | 4/1975 | Munnerlyn |
| 4,069,823 | A | 1/1978 | Isakov et al. |
| 4,438,765 | A | 3/1984 | Wilinsky |
| 4,443,075 | A | 4/1984 | Crane |
| 4,523,821 | A | 6/1985 | Lang et al. |
| 4,579,430 | A | 4/1986 | Bille |
| 4,632,528 | A | 12/1986 | Yoshino et al. |
| 4,669,466 | A | 6/1987 | L'Esperance |

(List continued on next page.)

FOREIGN PATENT DOCUMENTS

| DE | 24 50 095 A1 | 4/1976 |
| DE | 42 22 395 A1 | 1/1994 |
| DE | 199 26 476 A1 | 12/2000 |

(List continued on next page.)

OTHER PUBLICATIONS

Liang, et al, "Objective Measurement of Wave Aberrations of the Human Eye with the Use of a Hartmann–Shack Wave–front Sensor," *J. Opt. Soc. Am. A*, vol. 11, No. 7, Jul. 1994, pp. 1949–1957.

(List continued on next page.)

*Primary Examiner*—David M. Shay
(74) *Attorney, Agent, or Firm*—Allen, Dyer, Doppelt, Milbrath & Gilchrist, P.A.

(57) ABSTRACT

An ophthalmic laser system includes a laser beam delivery system and an eye tracker responsive to movement of the eye operable with a laser beam delivery system for ablating corneal material of the eye through placement of laser beam shot on a selected area of the cornea of the eye. The shots are fired in a sequence and pattern such that no laser shots are fired at consecutive locations and no consecutive shots overlap. The pattern is moved in response to the movement of the eye.

12 Claims, 4 Drawing Sheets

U.S. PATENT DOCUMENTS

| | | |
|---|---|---|
| 4,688,941 A | 8/1987 | Philbert |
| 4,702,245 A | 10/1987 | Schroder et al. |
| 4,718,418 A | 1/1988 | L'Esperance, Jr. |
| 4,721,379 A | 1/1988 | L'Esperance |
| 4,729,372 A | 3/1988 | L'Esperance, Jr. |
| 4,750,818 A | 6/1988 | Cochran |
| 4,759,615 A | 7/1988 | Bainbridge et al. |
| 4,764,930 A | 8/1988 | Bille et al. |
| 4,838,679 A | 6/1989 | Bille |
| 4,848,340 A | 7/1989 | Bille et al. |
| 4,881,808 A | 11/1989 | Bille et al. |
| 4,901,718 A | 2/1990 | Bille et al. |
| 4,907,586 A | 3/1990 | Bille et al. |
| 4,941,093 A | 7/1990 | Marshall et al. |
| 4,972,836 A | 11/1990 | Schenck et al. |
| 4,988,348 A | 1/1991 | Bille |
| 4,991,953 A | 2/1991 | Pflibsen et al. |
| 5,026,977 A | 6/1991 | Hubbard, Jr. |
| 5,048,946 A | 9/1991 | Sklar et al. |
| 5,057,102 A | 10/1991 | Tomioka et al. |
| 5,062,702 A | 11/1991 | Bille |
| 5,098,426 A | 3/1992 | Sklar et al. |
| 5,106,183 A | 4/1992 | Yoder, Jr. |
| 5,114,628 A | 5/1992 | Hofer et al. |
| 5,139,022 A | 8/1992 | Lempert |
| 5,147,352 A | 9/1992 | Azema et al. |
| 5,159,361 A | 10/1992 | Cambier et al. |
| 5,177,511 A | 1/1993 | Feuerstein et al. |
| 5,178,617 A | 1/1993 | Kuizenga et al. |
| 5,184,157 A | 2/1993 | Ichihashi et al. |
| 5,188,632 A * | 2/1993 | Goldenberg .................. 606/7 |
| 5,196,006 A | 3/1993 | Klopotek et al. |
| 5,198,845 A | 3/1993 | Triller |
| 5,202,709 A | 4/1993 | Ichihashi et al. |
| 5,214,456 A | 5/1993 | Gersten |
| 5,221,834 A | 6/1993 | Lisson et al. |
| 5,229,889 A | 7/1993 | Kittell |
| 5,233,174 A | 8/1993 | Zmek |
| 5,243,367 A | 9/1993 | Spellitz |
| 5,246,435 A | 9/1993 | Bille et al. |
| 5,258,791 A | 11/1993 | Penney et al. |
| 5,263,950 A | 11/1993 | L'Esperance, Jr. |
| 5,279,611 A | 1/1994 | McDonnell et al. |
| 5,293,871 A | 3/1994 | Reinstein et al. |
| 5,298,971 A | 3/1994 | Huang et al. |
| 5,302,979 A | 4/1994 | Maeda et al. |
| 5,307,097 A | 4/1994 | Baker |
| 5,324,281 A | 6/1994 | Muller |
| 5,329,544 A | 7/1994 | Shachrai et al. |
| 5,331,131 A | 7/1994 | Opdyke |
| 5,334,190 A | 8/1994 | Seiler |
| 5,339,121 A | 8/1994 | Shimmick et al. |
| 5,345,281 A | 9/1994 | Taboada et al. |
| 5,350,374 A | 9/1994 | Smith |
| 5,360,424 A | 11/1994 | Klopotek |
| 5,395,356 A | 3/1995 | King et al. |
| 5,404,884 A | 4/1995 | Lempert |
| 5,410,376 A | 4/1995 | Cornsweet et al. |
| 5,411,501 A | 5/1995 | Klopotek |
| 5,423,801 A | 6/1995 | Marshall et al. |
| 5,437,658 A | 8/1995 | Muller et al. |
| 5,439,462 A | 8/1995 | Bille et al. |
| 5,442,412 A | 8/1995 | Frey et al. |
| 5,452,031 A | 9/1995 | Ducharme |
| 5,461,212 A | 10/1995 | Seiler et al. |
| 5,473,392 A | 12/1995 | Klopotek |
| 5,474,548 A | 12/1995 | Knopp et al. |
| 5,475,452 A | 12/1995 | Kuhn et al. |
| 5,491,524 A | 2/1996 | Hellmuth et al. |
| 5,493,391 A | 2/1996 | Neal et al. |
| 5,502,518 A | 3/1996 | Lieberman |
| 5,505,723 A | 4/1996 | Muller |
| 5,507,741 A | 4/1996 | L'Esperance, Jr. |
| 5,512,965 A | 4/1996 | Snook |
| 5,512,966 A | 4/1996 | Snook |
| 5,521,657 A | 5/1996 | Klopotek |
| 5,548,354 A | 8/1996 | Kasahara et al. |
| 5,556,395 A | 9/1996 | Shimmick et al. |
| 5,563,709 A | 10/1996 | Poultney |
| 5,570,142 A | 10/1996 | Lieberman |
| 5,581,347 A | 12/1996 | Le Saux et al. |
| 5,592,246 A | 1/1997 | Kuhn et al. |
| 5,629,765 A | 5/1997 | Schmutz |
| 5,632,282 A | 5/1997 | Hay et al. |
| 5,632,742 A | 5/1997 | Frey et al. |
| 5,673,096 A | 9/1997 | Dorsel et al. |
| 5,684,545 A | 11/1997 | Dou et al. |
| 5,711,762 A | 1/1998 | Trokel |
| 5,722,427 A | 3/1998 | Wakil et al. |
| 5,735,283 A | 4/1998 | Snook |
| 5,735,843 A | 4/1998 | Trokel |
| 5,740,803 A | 4/1998 | Gray et al. |
| 5,757,463 A | 5/1998 | Kohayakawa |
| 5,777,719 A | 7/1998 | Williams et al. |
| 5,784,146 A | 7/1998 | Nanjo et al. |
| 5,785,704 A | 7/1998 | Bille et al. |
| 5,822,035 A | 10/1998 | Bille |
| 5,825,476 A | 10/1998 | Abitol et al. |
| 5,841,511 A | 11/1998 | D'Souza et al. |
| 5,847,804 A | 12/1998 | Sarver et al. |
| 5,861,955 A | 1/1999 | Gordon |
| 5,864,381 A | 1/1999 | Neal et al. |
| 5,865,832 A * | 2/1999 | Knopp et al. .................. 606/10 |
| 5,920,373 A | 7/1999 | Bille |
| 5,936,720 A | 8/1999 | Neal et al. |
| 5,943,117 A | 8/1999 | Van De Velde |
| 5,949,521 A | 9/1999 | Williams et al. |
| 5,963,300 A | 10/1999 | Horwitz |
| 5,966,197 A | 10/1999 | Yee |
| 5,993,441 A | 11/1999 | Muller et al. |
| 5,994,687 A | 11/1999 | Chanteloup et al. |
| 6,007,204 A | 12/1999 | Fahrenkrug et al. |
| 6,043,885 A | 3/2000 | Mazuet et al. |
| 6,050,687 A | 4/2000 | Bille et al. |
| 6,057,913 A | 5/2000 | Brown et al. |
| 6,086,204 A | 7/2000 | Magnante |
| 6,095,651 A | 8/2000 | Williams et al. |
| 6,155,684 A | 12/2000 | Bille et al. |

FOREIGN PATENT DOCUMENTS

| | | |
|---|---|---|
| EP | 0 151 869 A2 | 8/1985 |
| EP | 0 697 611 A2 | 2/1996 |
| EP | 0 697 611 A3 | 2/1996 |
| JP | 5-146409 | 6/1993 |
| JP | 6-327634 | 11/1994 |
| WO | WO 85/01869 | 5/1985 |
| WO | WO 87/05205 | 9/1987 |
| WO | WO 87/06478 | 11/1987 |
| WO | WO 92/01417 | 2/1992 |
| WO | WO 92/21999 | 12/1992 |
| WO | WO 93/16631 | 9/1993 |
| WO | WO 95/28989 | 11/1995 |
| WO | WO 98/27863 | 7/1998 |

OTHER PUBLICATIONS

Wu, "Supernormal Vision, a Focus on Adaptive Optics Improves Images of the Eye and Boosts Vision," *Science News*, vol. 152, Nov. 15, 1997, pp. 312–313.

Dreher, et al., "Active Optical Depth Resolution Improvement of the Laser Tomographic Scanner," *Applied Optics*, vol. 28, No. 4, Feb. 1989, pp. 804–808.

Geary, "Appendix 1.1—Basic Geometrical Optics, Chapter 6—Indirect Wavefront Measurement, Part II," and "Chapter 7—Wavefront Sensor Characterization & Calibration," *Introduction to Wavefront Sensors*, May 1995, pp. 10–11, 89–103, and 105–109.

"Scientists Snap Sharpest Pictures of Living Human Retina," http://www.rochester.edu/pr/releases/opt/will.htm, Oct. 3, 1994.

The Applied Optics Group, "Shack Hartmann Sensors," http://op.ph.ic.ac.uk/ao/sh sense.html, Jun. 4, 1996, pp. 1–3.

The Applied Optics Group, "Results from UKIRT," http://op.ph.ic.ac.uk/ao/ukirt res.html, Feb. 22, 1995, pp. 1–2.

The Applied Optics Group, "Astronomical Imaging Through Turbulence: An Overview," http://op.ph.ic.ac.uk/ao/overview.html, Jun. 4, 1996, pp. 1–4.

.cESA, WFS, "Wave Front Sensor," http://esapub.esrin.esa.it/pointtotest/test251.html, May 23, 1997, pp. 1–2.

Williams, "Limits of Human Vision," http://www.cvs.rochester.edu/people/d williams/d williams.html, Dec. 30, 1998, pp. 1–4.

"Extensions of Low–Cost Adaptive Optics: Imaging of Space–Objects, the Retina, and Power Projection," Industrial Sensors and Actuators, dated Dec. 1993 (actual publication date, if any, unknown), pp. 1, 10, and 15.

Labjuhn, et al., Astigmatismuskorrektur durch Laser-thermokeratoplastik (LTK)—Ein Ansatz Für dieKorrektur des hohen Astigmatismus nach Perforierender Keratoplastik, *Contactologia 18D* (1996), pp. 175–183.

Cohen, et al., "Assessment of the Power and Height of Radial Aspheres Reported by a Computer–assisted Keratoscope," *American Journal of Ophthalmology*, vol. 119, vol. No. 6, Nov. 30, 1994, pp. 723–732.

Corbett, et al., "The Topography of the Normal Cornea," *Eur J Implant Ref Surg.*, vol. 6, Oct., 1994, pp. 286–297.

Maeder, et al., "Accurate 3D Corneal Surface Measurement Using an Automated Mapping Approach," APIE, vol. 2434, 1995, pp. 328–334.

Salmon, et al., "Comparison of Elevation, Curvature, and Power Decriptors for Corneal Topographic Mapping," *Optometry & Vision Sciences*, vol. 72, No. 11, 1195, pp. 800–808.

Pavlopoulos, et al, "The Effect of Artificial Tears on Computer–assisted Corneal Topograpy in Normal Eyes and After Penetrating Keratoplasty," *American Journal of Ophthalmology*, vol. 119, Jun. 1995, pp. 712–722.

Roberts, "Characterization of the Inherent Error in a Spherically–Biased Corneal Topography System in Mapping a Radially Aspheric Surface," *Journal of Refractive & Corneal Surgery*, vol. 10, Mar./Apr. 1994, pp. 103–111.

Thornton, "Clinical Evaluation of Corneal Topography," *J. Cataract Refract. Surg.*, vol. 19, Supplement 1993, pp. 198–202.

Rabinowitz, et al., "Computer–assisted corneal Topography in Keratoconus," *Refractive & Corneal Surgery*, vol. 5, Nov./Dec. 1989, pp. 400–408.

Wilson, et al., "Accuracy and Precision of the Corneal Analysis System and the Topographic Modeling System," *Cornea*, vol. 11, No. 1, 1992, pp. 28–35.

Bogan, et al., Computer–assisted Videokeratography of Corneal Topography After Radial Keratotomy, *Arch. Ophthalmol.*, vol. 109, Jun. 1991, pp. 834–841.

Bogan, et al., "Classification of Normal Corneal Topography Based on Computer–assisted Videokeratogrpahy," *Arch. Ophthalmol.*, vol. 108, Jul. 1990, pp. 945–949.

Reidy, et al., "The Corneal Topography of Epikeratophakia," *Refractive & Corneal Surgery*, vol. 6, Jan./Feb. 1990, pp. 26–31.

Dingeldein, et al., "The Topography of Normal Corneas," *Arch. Ophthalmol*, vol. 107, Apr. 1989, pp. 512–518.

McDonnell, et al., "Topographic Analysis and Visual Acuity After Radial Keratotomy," *American Journal of Ophthalmology*, vol. 106, No. 6, Dec. 1988, pp. 692–695.

McDonnell, et al., "Corneal Topographic Changes After Radial Keratotomy," *Ophthalmology*, vol. 96, No. 1, Jan. 1989, pp. 45–49.

Kiely, et al., "The Mean Shape of the Human Cornea," *Optica Acta*, vol. 29, No. 8, 1982, pp. 1027–1040.

Bafna, et al., "Corneal Power Calculated by the Paraxial Formula and Snell's Law in Normal Corneas," *Investigative Ophthalmology & Visual Science*, vol. 37, No. 3, Feb. 1996, Poster No. 2589.

Matallana, et al., "3–D Video Corneal Topography True Elevation Mapping," *Investigative Ophthalmology & Visual Science*, vol. 37, No. 3, Feb. 1996, Poster No. 2590.

Aoyama, et al, "Quantitative Evaluation of Corneal Astigmatism Using Computer Corneal Topography and Newly Developed Software," *Investigative Ophthalmology & Visual Science*, vol. 37, No. 3, Feb. 1996, Poster No. 2591.

Celikkol, et al, "Neural Network Analysis of Videokeratography Following Excimer Laser Photorefractive Keratectomy," *Investigative Ophthalmology & Visual Science*, vol. 37, No. 3, Feb. 1996, Poster No. 2592.

Walsh, et al., "Objective Technique for the Determination of Monochromatic Aberrations of the Human Eye," *J. Opt. Soc. Am. A*, vol. 1, No. 9, Sep. 1984, pp. 987–992.

Williams, et al., "Adaptive Optics for High Resolution Retinal Imaging," *Investigative Ophthalmology & Visual Science*, vol. 37, No. 3, Feb. 1996, p. 1055.

Charman, "Wavefront Aberration of the Eye: A Review," *Optometry and Vision Science*, vol. 68, No. 8, pp. 574–583.

Bartsch, et al., "Resolution Improvement in Confocal Scanning Laser Tomography of the Human Fundus," *1994 Technical Digest Series*, vol. 2 (Optical Society of America, Washington, D. C.), 1994, pp. 134–137.

Dreher, et al., "Active Optical Depth Resolution Improvement of the Laser Tomographic Scanner," *Applied Optics*, vol. 28, No. 4, Feb. 1989, pp. 804–808.

Bille, et al., "Scanning Laser Tomography of the Living Human Eye," *Noninvasive Diagnostic Techniques in Ophthalmology*, Chapter 28, edited by Masters, B.R., Springer–Verlag, 1990, pp. 528–547.

Liang, Junzhong, *A New Method to Precisely Measure the Wave Aberrations of the Human Eye with a Hartmann-–Shack Wavefront Sensor*, Inaugural Dissertation, Dec. 1991, pp. 1–115, Heidelberg, Germany.

Bille, et al., "Imaging of the Retina by Scanning Laser Tomography," *New Methods in Microscopy and Low Light Imaging*, vol. 1161, 1989, pp. 417–425.

Cubalchini, "Modal Wave–front Estimation from Phase Derivative Measurements," *J. Opt. Soc. Am.*, vol. 69, 1979, pp. 972–977.

"Modal Wave–front Estimation from Phase Derivative Measurements," Referenced in Bille, U.S. patent No. 5,062,702, IDS, 1990.

Freischlad, et al., "Modal Estimation of a Wave Front from Difference Measurements Using the Discrete Fourier Transform," *J. Opt. soc. Am.*, vol. 3, No. 11, Nov. 1986, pp. 1852–1861.

Klyce, et al., "Imaging, Reconstruction, and Display of Corneal Topography," *New Methods in Microscopy and Low Light Imaging*, vol. 1161, 1989, pp. 409–416.

Baker, "Optical Surface Testing of the Cornea," *New Methods in Microscopy and Low Light Imaging*, vol. 1161, 1989, pp. 427–437.

Southwell, "Wave–front Estimation from Wave–front Slope Measurements," *J. Opt. Soc. Am.*, vol. 70, No. 8, Aug. 1980, pp. 998–1005.

Gailitis et al, Solid State Ultraviolet Laser Ablation of the Cornea and Synthetic Collagen Lenticules, vol. 105, Sep. 1987, pp. 566–562.

* cited by examiner

METHOD OF CORRECTING VISION

CROSS-REFERENCE TO RELATED APPLICATIONS

This application is a continuation of and incorporates by reference application Ser. Nos. 09/376,133, filed Aug. 17, 1999, which is a continuation of application Ser. No. 08/232,615, filed Apr. 25, 1994, now issued as U.S. Pat. No. 5,980,513, and further incorporates U.S. Pat. Nos. 5,849,006 and 5,632,742 by reference, all of which are commonly owned and have the disclosures incorporated by reference.

FIELD OF THE INVENTION

The invention relates generally to laser systems, and more particularly to a laser system used to erode a moving surface such as an eye's corneal tissue.

BACKGROUND OF THE INVENTION

Use of lasers to erode all or a portion of a workpiece's surface is known in the art. In the field of ophthalmic medicine, photorefractive keratectomy (PRK) is a procedure for laser correction of focusing deficiencies of the eye by modification of corneal curvature. PRK is distinct from the use of laser-based devices for more traditional ophthalmic surgical purposes, such as tissue cutting or thermal coagulation. PRK is generally accomplished by use of a 193 nanometer wavelength excimer laser beam that ablates away the workpiece, i.e., corneal tissue, in a photo decomposition process. Most clinical work to this point has been done with a laser operating at a fluence level of 120–195 mJ/cm$^2$ and a pulse-repetition rate of approximately 5–10 Hz. The procedure has been referred to as "corneal sculpting."

Before sculpting of the cornea takes place, the epithelium or outer layer of the cornea is mechanically removed to expose Bowman's membrane on the anterior surface of the stroma. At this point, laser ablation at Bowman's layer can begin. An excimer laser beam is preferred for this procedure. The beam may be variably masked during the ablation to remove corneal tissue to varying depths as necessary for recontouring the anterior stroma. Afterward, the epithelium rapidly regrows and resurfaces the contoured area, resulting in an optically correct (or much more nearly so) cornea. In some cases, a surface flap of the cornea is folded aside and the exposed surface of the cornea's stroma is ablated to the desired surface shape with the surface flap then being replaced.

Phototherapeutic keratectomy (PTK) is a procedure involving equipment functionally identical to the equipment required for PRK. The PTK procedure differs from PRK in that rather than reshaping the cornea, PTK uses the aforementioned excimer laser to treat pathological superficial, corneal dystrophies, which might otherwise require corneal transplants.

In both of these procedures, surgical errors due to application of the treatment laser during unwanted eye movement can degrade the refractive outcome of the surgery. The eye movement or eye positioning is critical since the treatment laser is centered on the patient's theoretical visual axis which, practically-speaking, is approximately the center of the patient's pupil. However, this visual axis is difficult to determine due in part to residual eye movement and involuntary eye movement known as saccadic eye movement. Saccadic eye movement is high-speed movement (i.e., of very short duration, 10–20 milliseconds, and typically up to 1° of eye rotation) inherent in human vision and is used to provide dynamic scene to the retina. Saccadic eye movement, while being small in amplitude, varies greatly from patient to patient due to psychological effects, body chemistry, surgical lighting conditions, etc. Thus, even though a surgeon may be able to recognize some eye movement and can typically inhibit/restart a treatment laser by operation of a manual switch, the surgeon's reaction time is not fast enough to move the treatment laser in correspondence with eye movement.

SUMMARY OF THE INVENTION

Accordingly, it is an object of the present invention to provide a laser beam delivery and eye tracking method and system that is used in conjunction with a laser system capable of eroding a surface.

Another object of the present invention is to provide a system for delivering a treatment laser to a surface and for automatically redirecting the treatment laser to compensate for movement of the surface.

Still another object of the present invention is to provide a system for delivering a corneal ablating laser beam to the surface of an eye in a specific pattern about the optical center of the eye, and for automatically redirecting the corneal ablating laser beam to compensate for eye movement such that the resulting ablating pattern is the same regardless of eye movement.

Yet another object of the present invention is to provide a laser beam delivery and eye tracking system for use with an ophthalmic treatment laser where the tracking operation detects eye movement in a non-intrusive fashion.

A further object of the present invention is to provide a laser beam delivery and eye tracking system for automatically delivering and maintaining a corneal ablating laser beam with respect to the geometric center of an eye's pupil or a doctor defined offset from the center of the eye's pupil. A special object of this invention is the use of the laser pulses which are distributed in a pattern of discrete ablations to shape objects other than for corneal ablating.

Other objects and advantages of the present invention will become more obvious hereinafter in the specification and drawings.

In accordance with the present invention, an eye treatment laser beam delivery and eye tracking system is provided. A treatment laser and its projection optics generate laser light along an original beam path (i.e., the optical axis of the system) at an energy level suitable for treating the eye. An optical translator shifts the original beam path in accordance with a specific scanning pattern so that the original beam is shifted onto a resulting beam path that is parallel to the original beam path. An optical angle adjuster changes the resulting beam path's angle relative to the original beam path such that the laser light is incident on the eye.

An eye movement sensor detects measurable amounts of movement of the eye relative to the system's optical axis and then generates error control signals indicative of the movement. The eye movement sensor includes 1) a light source for generating light energy that is non-damaging with respect to the eye, 2) an optical delivery arrangement for delivering the light energy on a delivery light path to the optical angle adjuster in a parallel relationship with the resulting beam path of the treatment laser, and 3) an optical receiving arrangement. The parallel relationship between the eye movement sensor's delivery light path and the treatment laser's resulting beam path is maintained by the optical angle adjuster. In this way, the treatment laser light and the eye movement sensor's light energy are incident on the eye in their parallel relationship.

A portion of the eye movement sensor's light energy is reflected from the eye as reflected energy traveling on a reflected light path back through the optical angle adjuster. The optical receiving arrangement detects the reflected energy and generates the error control signals based on the reflected energy. The optical angle adjuster is responsive to the error control signals to change the treatment laser's resulting beam path and the eye movement sensor's delivery light path in correspondence with one another. In this way, the beam originating from the treatment laser and the light energy originating from the eye movement sensor track along with the eye's movement.

In carrying out this technique, the pattern constitutes overlapping but not coaxial locations for ablation to occur with each pulse removing a microvolume of material by ablation or erosion. For different depths, a pattern is repeated over those areas where increased ablation is needed. The laser pulses are usually at a certain pulse repetition rate. The subsequent pulses in a sequence are spaced at least one pulse beam width from the previous pulse and at a distance the ablated particles will not substantially interfere with the subsequent pulse. In order to maximize the speed of the ablation, the subsequent pulse is spaced sufficiently close to enable the beam to be moved to the successive location within the time of the pulse repetition. The ablation is carried out on an object until a desired specific shape is achieved.

This technique is fundamentally new and may be used on objects other than corneas.

DETAILED DESCRIPTION OF THE INVENTION

Figure 1:
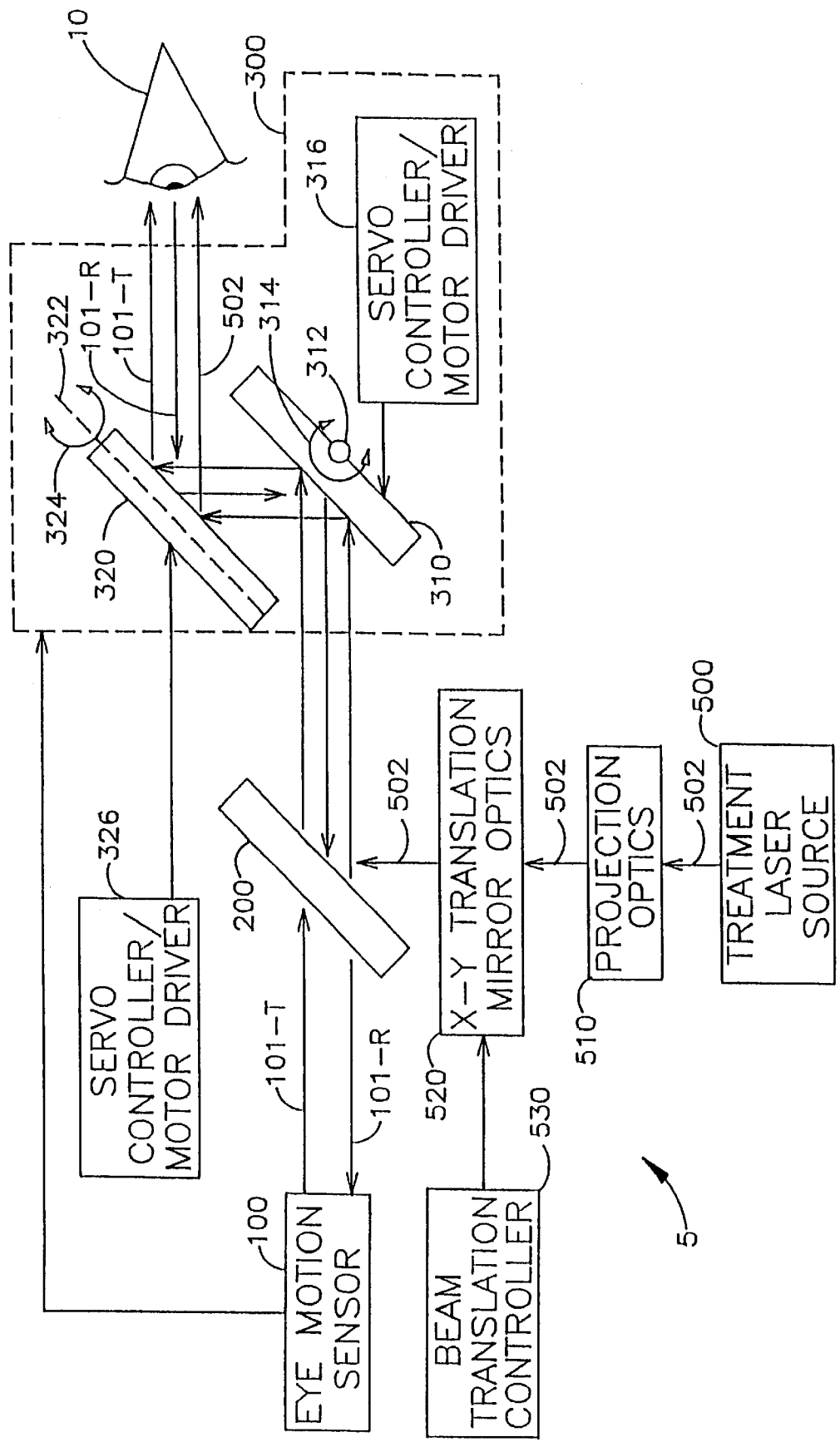
FIG. 1 is a block diagram of a laser beam delivery and eye tracking system in accordance with the present invention as it would be used in conjunction with an ophthalmic treatment laser.

Referring now to the drawings, and more particularly to FIG. 1, a block diagram is shown of a laser beam delivery and eye tracking system referenced generally by the numeral 5. The laser beam delivery portion of system 5 includes treatment laser source 500, projection optics 510, X-Y translation mirror optics 520, beam translation controller 530, dichroic beamsplitter 200, and beam angle adjustment mirror optics 300. By way of example, it will be assumed that treatment laser 500 is a 193 nanometer wavelength excimer laser used in an ophthalmic PRK (or PTK) procedure performed on a movable workpiece, e.g., eye 10. However, it is to be understood that the method and system of the present invention will apply equally as well to movable workpieces other than an eye, and further to other wavelength surface treatment or surface eroding lasers. The laser pulses are distributed as shots over the area to be ablated or eroded, preferably in a distributed sequence. A single laser pulse of sufficient power to cause ablation creates a micro cloud of ablated particles which interferes with the next laser pulse if located in the same or immediate point. To avoid this interference, the next laser pulse is spatially distributed to a next point of erosion or ablation that is located a sufficient distance so as to avoid the cloud of ablated particles. Once the cloud is dissipated, another laser pulse is made adjacent the area being eroded so that after the pattern of shots is completed the cumulative shots fill in and complete said pattern so that the desired shape of the object or cornea is achieved.

Figure 2:
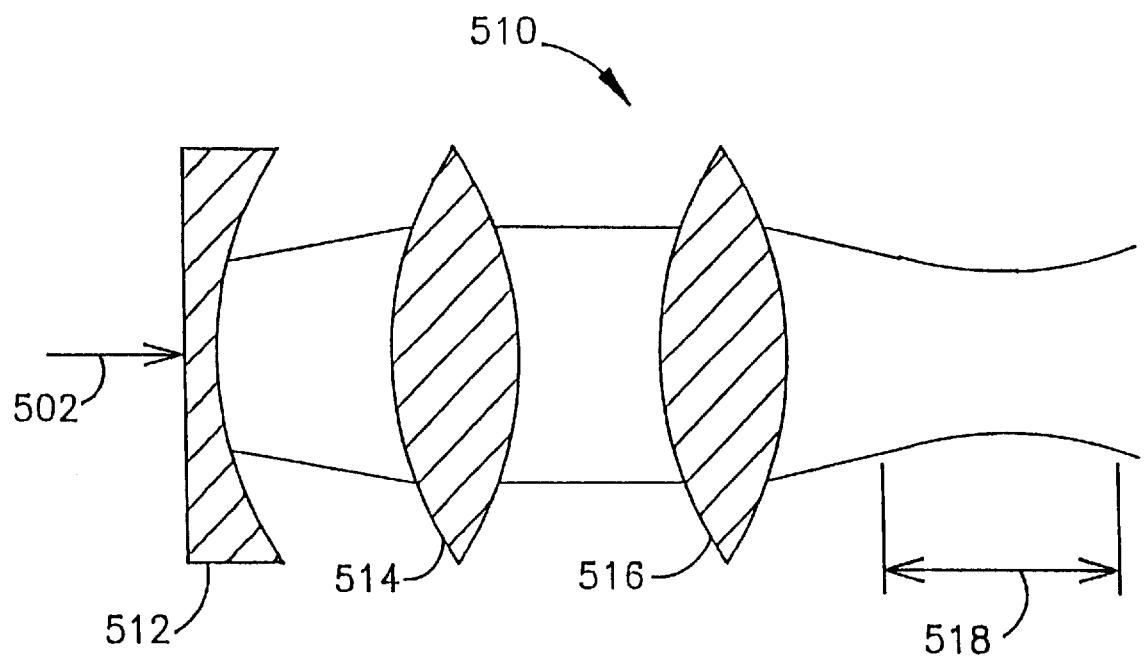
FIG. 2 is a sectional view of the projection optics used with the ophthalmic treatment laser embodiment of the laser beam delivery portion of the present invention.

In operation of the beam delivery portion of system 5, laser source 500 produces laser beam 502 which is incident upon projection optics 510. Projection optics 510 adjusts the diameter and distance to focus of beam 502 depending on the requirements of the particular procedure being performed. For the illustrative example of an excimer laser used in the PRK or PTK procedure, projection optics 510 includes planar concave lens 512, and fixed focus lenses 514 and 516 as shown in the sectional view of FIG. 2. Lenses 512 and 514 act together to form an afocal telescope that expands the diameter of beam 502. Fixed focus lens 516 focuses the expanded beam 502 at the workpiece, i.e., eye 10, and provides sufficient depth, indicated by arrow 518, in the plane of focus of lens 516. This provides flexibility in the placement of projection optics 510 relative to the surface of the workpiece. An alternative implementation is to eliminate lens 514 when less flexibility can be tolerated.

After exiting projection optics 510, beam 502 impinges on X-Y translation mirror optics 520 where beam 502 is translated or shifted independently along each of two orthogonal translation axes as governed by beam translation controller 530. Controller 530 is typically a processor programmed with a predetermined set of two-dimensional translations or shifts of beam 502 depending on the particular ophthalmic procedure being performed. For the illustrative example of the excimer laser used in a PRK or PTK procedure, controller 530 may be programmed in accordance with the aforementioned copending patent application entitled "Laser Sculpting System and Method". The programmed shifts of beam 502 are implemented by X-Y translation mirror optics 520.

Figure 3:
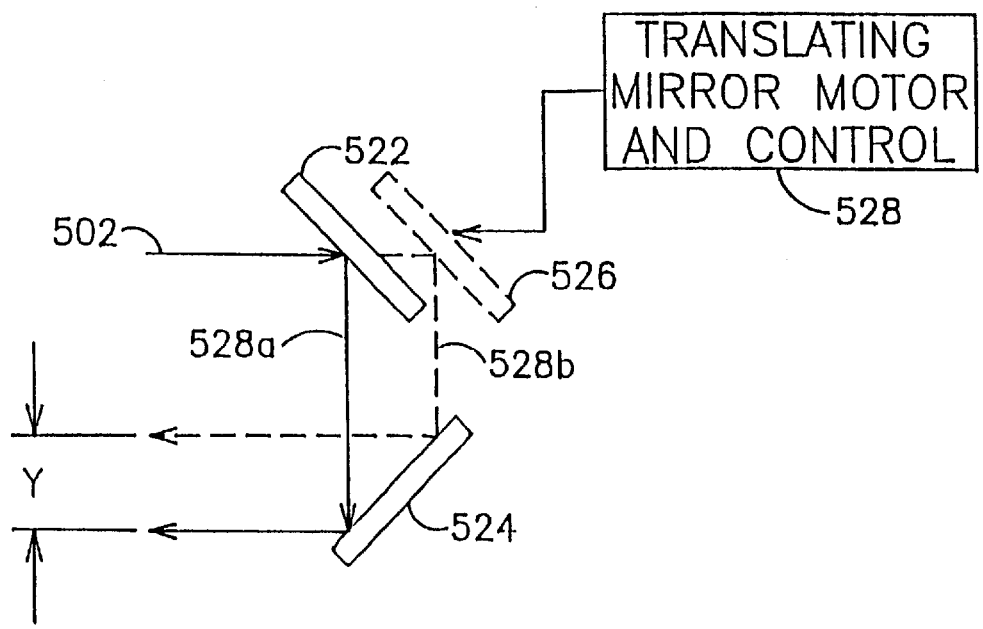
FIG. 3 illustrates diagrammatically an optical arrangement of mirrors used to produce translational shifts in a light beam along one axis.

Each X and Y axis of translation is independently controlled by a translating mirror. As shown diagrammatically in FIG. 3, the Y-translation operation of X-Y translation mirror optics 520 is implemented using translating mirror 522. Translating mirror 522 is movable between the position shown and the position indicated by dotted line 526. Movement of translating mirror 522 is such that the angle of the output beam with respect to the input beam remains constant. Such movement is brought about by translation mirror motor and control 525 driven by inputs received from beam translation controller 530. By way of example, motor and control 525 can be realized with a motor from Trilogy Systems Corporation (e.g., model T050) and a control board from Delta Tau Systems (e.g., model 400-602276 PMAC).

With translating mirror 522 positioned as shown, beam 502 travels the path traced by solid line 528a. With translating mirror 522 positioned along dotted line 526, beam 502 travels the path traced by dotted line 528b. A similar translating mirror (not shown) would be used for the X-translation operation. The X-translation operation is accomplished in the same fashion but is orthogonal to the Y-translation. The X-translation may be implemented prior or subsequent to the Y-translation operation.

The eye tracking portion of system 5 includes eye movement sensor 100, dichroic beamsplitter 200 and beam angle adjustment mirror optics 300. Sensor 100 determines the amount of eye movement and uses same to adjust mirrors 310 and 320 to track along with such eye movement. To do this, sensor 100 first transmits light energy 101-T which has been selected to transmit through dichroic beamsplitter 200. At the same time, after undergoing beam translation in accordance with the particular treatment procedure, beam 502 impinges on dichroic beamsplitter 200 which has been selected to reflect beam 502 (e.g., 193 nanometer wavelength laser beam) to beam angle adjustment mirror optics 300.

Light energy 101-T is aligned such that it is parallel to beam 502 as it impinges on beam angle adjustment mirror optics 300. It is to be understood that the term "parallel" as used herein includes the possibility that light energy 101-T and beam 502 can be coincident or collinear. Both light energy 101-T and beam 502 are adjusted in correspondence with one another by optics 300. Accordingly, light energy 101-T and beam 502 retain their parallel relationship when they are incident on eye 10. Since X-Y translation mirror optics 520 shifts the position of beam 502 in translation independently of optics 300, the parallel relationship between beam 502 and light energy 101-T is maintained throughout the particular ophthalmic procedure.

Beam angle adjustment mirror optics consists of independently rotating mirrors 310 and 320. Mirror 310 is rotatable about axis 312 as indicated by arrow 314 while mirror 320 is rotatable about axis 322 as indicated by arrow 324. Axes 312 and 322 are orthogonal to one another. In this way, mirror 310 is capable of sweeping light energy 101-T and beam 502 in a first plane (e.g., elevation) while mirror 320 is capable of independently sweeping light energy 101-T and beam 502 in a second plane (e.g., azimuth) that is perpendicular to the first plane. Upon exiting beam angle adjustment mirror optics 300, light energy 101-T and beam 502 impinge on eye 10.

Figure 4:
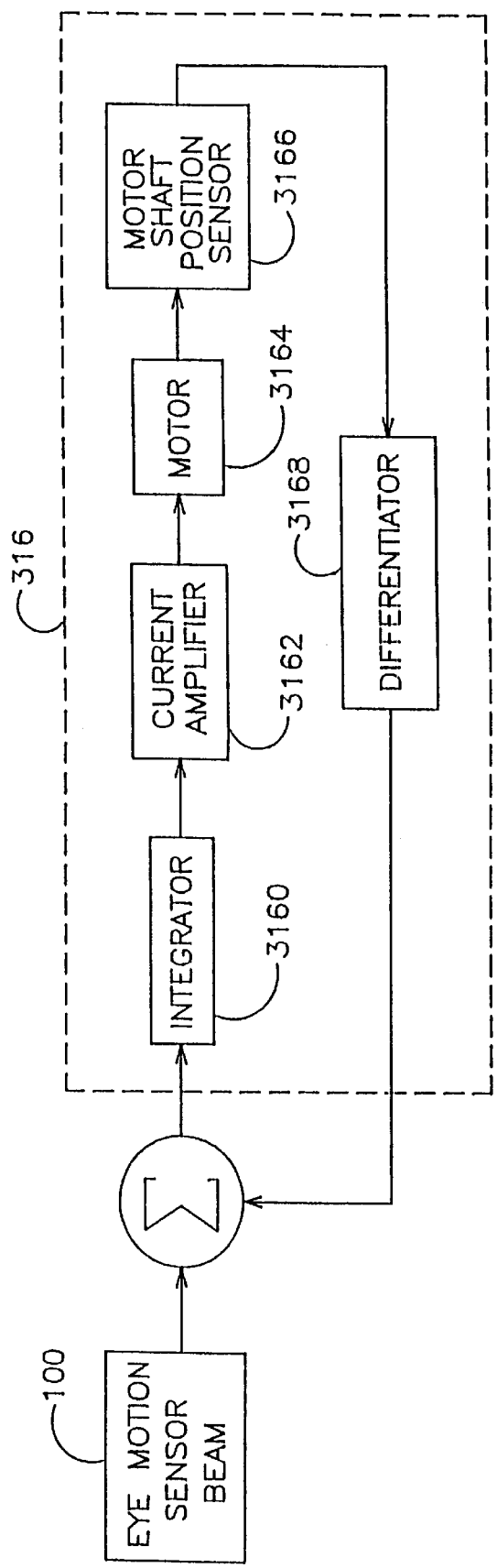
FIG. 4 is a block diagram of the servo controller/motor driver circuitry used in the ophthalmic treatment laser embodiment of the present invention.

Movement of mirrors 310 and 320 is typically accomplished with servo controller/motor drivers 316 and 326, respectively. FIG. 4 is a block diagram of a preferred embodiment servo controller/motor driver 316 used for the illustrative PRK/PTK treatment example. (The same structure is used for servo controller/motor driver 326.) In general, drivers 316 and 326 must be able to react quickly when the measured error from eye movement sensor 100 is large, and further must provide very high gain from low frequencies (DC) to about 100 radians per second to virtually eliminate both steady state and transient error.

More specifically, eye movement sensor 100 provides a measure of the error between the center of the pupil (or an offset from the center of the pupil that the doctor selected) and the location where mirror 310 is pointed. Position sensor 3166 is provided to directly measure the position of the drive shaft (not shown) of galvanometer motor 3164. The output of position sensor 3166 is differentiated at differentiator 3168 to provide the velocity of the drive shaft of motor 3164.

This velocity is summed with the error from eye movement sensor 100. The sum is integrated at integrator 3160 and input to current amplifier 3162 to drive galvanometer motor 3164. As the drive shaft of motor 3164 rotates mirror 310, the error that eye movement sensor 100 measures decreases to a negligible amount. The velocity feedback via position sensor 3166 and differentiator 3168 provides servo controller/motor driver 316 with the ability to react quickly when the measured sensor error is large.

Light energy reflected from eye 10, as designated by reference numeral 101-R, travels back through optics 300 and beamsplitter 200 for detection at sensor 100. Sensor 100 determines the amount of eye movement based on the changes in reflection energy 101-R. Error control signals indicative of the amount of eye movement are fed back by sensor 100 to beam angle adjustment mirror optics 300. The error control signals govern the movement or realignment of mirrors 310 and 320 in an effort to drive the error control signals to zero. In doing this, light energy 101-T and beam 502 are moved in correspondence with eye movement while the actual position of beam 502 relative to the center of the pupil is controlled by X-Y translation mirror optics 520.

In order to take advantage of the properties of beamsplitter 200, light energy 101-T must be of a different wavelength than that of treatment laser beam 502. The light energy should preferably lie outside the visible spectrum so as not to interfere or obstruct a surgeon's view of eye 10. Further, if the present invention is to be used in ophthalmic surgical procedures, light energy 101-T must be "eye safe" as defined by the American National Standards Institute (ANSI). While a variety of light wavelengths satisfy the above requirements, by way of example, light energy 101-T is infrared light energy in the 900 nanometer wavelength region. Light in this region meets the above noted criteria and is further produced by readily available, economically affordable light sources. One such light source is a high pulse repetition rate GaAs 905 nanometer laser operating at 4 kHz which produces an ANSI defined eye safe pulse of 10 nanojoules in a 50 nanosecond pulse.

Figure 5:
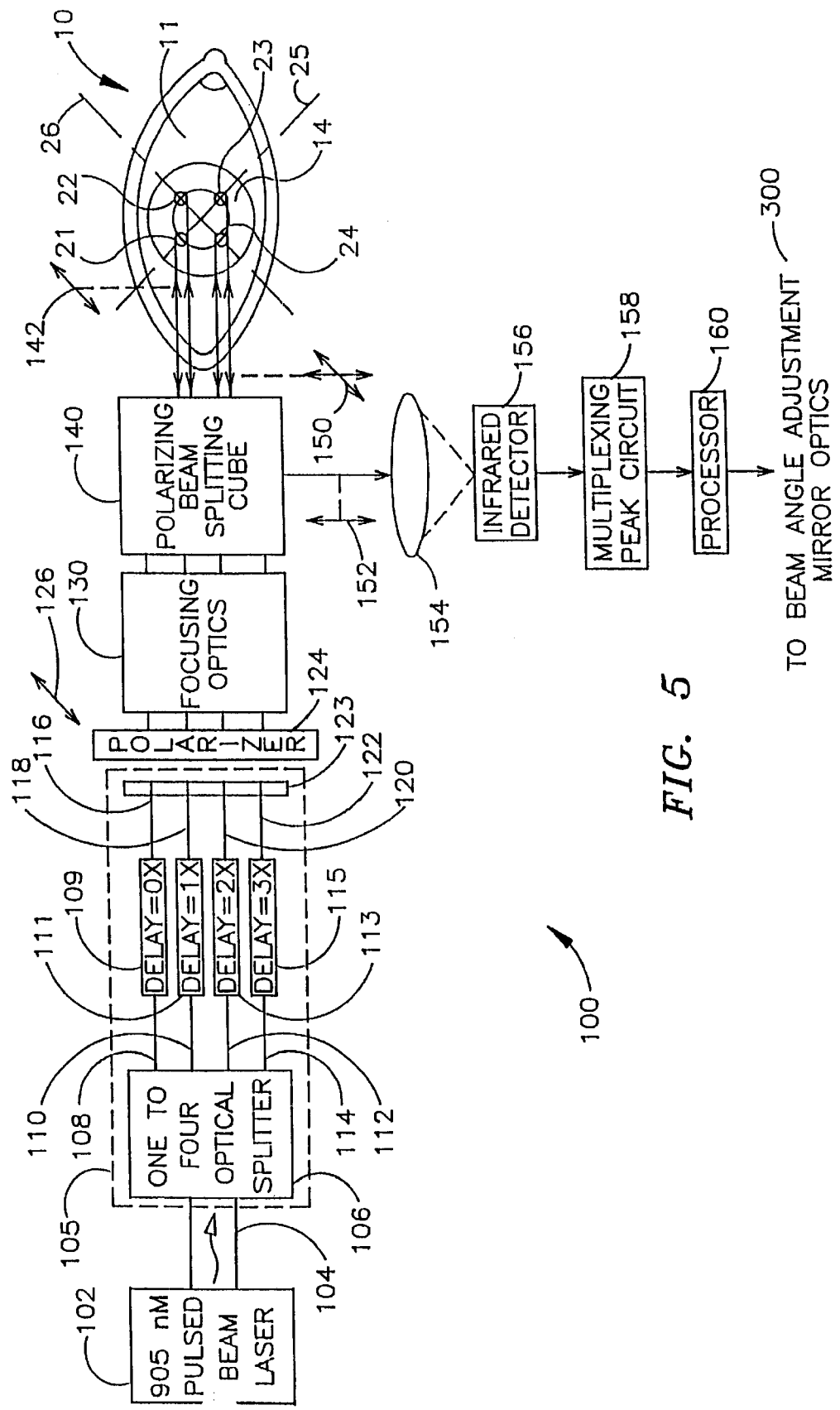
FIG. 5 is a block diagram of a preferred embodiment eye movement sensor used in the ophthalmic treatment laser embodiment of the present invention.

A preferred embodiment method for determining the amount of eye movement, as well as eye movement sensor 100 for carrying out such a method, are described in detail in the aforementioned copending patent application. However, for purpose of a complete description, sensor 100 will be described briefly with the aid of the block diagram shown in FIG. 5. Sensor 100 may be broken down into a delivery portion and a receiving portion. Essentially, the delivery portion projects light energy 101-T in the form of light spots 21, 22, 23 and 24 onto a boundary (e.g., iris/pupil boundary 14) on the surface of eye 10. The receiving portion monitors light energy 101-R in the form of reflections caused by light spots 21, 22, 23 and 24.

In delivery, spots 21 and 23 are focused and positioned on axis 25 while spots 22 and 24 are focused and positioned on axis 26 as shown. Axes 25 and 26 are orthogonal to one another. The four spots 21, 22, 23 and 24 are of equal energy and are spaced evenly about and on iris/pupil boundary 14. This placement provides for two-axis motion sensing in the following manner. Each light spot 21, 22, 23 and 24 causes a certain amount of reflection at its position on iris/pupil boundary 14. Since boundary 14 moves in coincidence with eye movement, the amount of reflection from light spots 21, 22, 23 and 24 changes in accordance with eye movement. By spacing the four spots evenly about the circular boundary geometry, horizontal or vertical eye movement is detected by changes in the amount of reflection from adjacent pairs of spots. For example, horizontal eye movement is monitored by comparing the combined reflection from light spots 21 and 24 with the combined reflection from light spots 22 and 23. In a similar fashion, vertical eye movement is monitored by comparing the combined reflection from light spots 21 and 22 with the combined reflection from light spots 23 and 24.

More specifically, the delivery portion includes a 905 nanometer pulsed diode laser 102 transmitting light through optical fiber 104 to an optical fiber assembly 105 that splits and delays each pulse from laser 102 into preferably four equal energy pulses. Assembly 105 includes one-to-four optical splitter 106 that outputs four pulses of equal energy into optical fibers 108, 110, 112, 114. In order to use a single processor to process the reflections caused by each pulse transmitted by fibers 108, 110, 112 and 114, each pulse is uniquely delayed by a respective fiber optic delay line 109, 111, 113 and 115. For example, delay line 109 causes a delay of zero, i.e., DELAY=0x where x is the delay increment; delay line 111 causes a delay of x, i.e., DELAY=1x; etc.

The pulse repetition frequency and delay increment x are chosen so that the data rate of sensor 100 is greater than the speed of the movement of interest. In terms of saccadic eye movement, the data rate of sensor 100 must be on the order of at least several hundred hertz. For example, a sensor data rate of approximately 4 kHz is achieved by 1) selecting a small but sufficient value for x to allow processor 160 to handle the data (e.g., 160 nanoseconds), and 2) selecting the time between pulses from laser 102 to be 250 microseconds (i.e., laser 102 is pulsed at a 4 kHz rate).

The four equal energy pulses exit assembly 105 via optical fibers 116, 118, 120 and 122 which are configured as a fiber optic bundle 123. Bundle 123 arranges the optical fibers such that the center of each fiber forms the corner of a square. Light from assembly 105 is passed through an optical polarizer 124 that outputs horizontally polarized light beams as indicated by arrow 126. Horizontally polarized light beams 126 pass to focusing optics 130 where spacing between beams 126 is adjusted based on the boundary of interest. Additionally, a zoom capability (not shown) can be provided to allow for adjustment of the size of the pattern formed by spots 21, 22, 23 and 24. This capability allows sensor 100 to adapt to different patients, boundaries, etc.

A polarizing beam splitting cube 140 receives horizontally polarized light beams 126 from focusing optics 130. Cube 140 is configured to transmit horizontal polarization and reflect vertical polarization. Accordingly, cube 140 transmits only horizontally polarized light beams 126 as indicated by arrow 142. Thus, it is only horizontally polarized light that is incident on eye 10 as spots 21, 22, 23 and 24. Upon reflection from eye 10, the light energy is depolarized (i.e., it has both horizontal and vertical polarization components) as indicated by crossed arrows 150.

The receiving portion first directs the vertical component of the reflected light as indicated by arrow 152. Thus, cube 140 serves to separate the transmitted light energy from the reflected light energy for accurate measurement. The vertically polarized portion of the reflection from spots 21, 22, 23 and 24, is passed through focusing lens 154 for imaging onto an infrared detector 156. Detector 156 passes its signal to a multiplexing peak detecting circuit 158 which is essentially a plurality of peak sample and hold circuits, a variety of which are well known in the art. Circuit 158 is configured to sample (and hold the peak value from) detector 156 in accordance with the pulse repetition frequency of laser 102 and the delay x. For example, if the pulse repetition frequency of laser 102 is 4 kHz, circuit 158 gathers reflections from spots 21, 22, 23 and 24 every 250 microseconds.

The values associated with the reflected energy for each group of four spots (i.e., each pulse of laser 102) are passed to a processor 160 where horizontal and vertical components of eye movement are determined. For example let R21, R22, R23 and R24 represent the detected amount of reflection from one group of spots 21, 22, 23 and 24, respectively. A quantitative amount of horizontal movement is determined directly from the normalized relationship $$\frac{(R_{21}+R_{24})-(R_{22}+R_{23})}{R_{21}+R_{22}+R_{23}+R_{24}}$$

while a quantitative amount of vertical movement is determined directly from the normalized relationship $$\frac{(R_{21}+R_{24})-(R_{23}+R_{24})}{R_{21}+R_{22}+R_{23}+R_{24}}$$

Note that normalizing (i.e., dividing by $R_{21}+R_{22}+R_{23}+R_{24}$) reduces the effects of variations in signal strength. Once determined the measured amounts of eye movement are sent to beam angle adjustment mirror optics 300.

The advantages of the present invention are numerous. Eye movement is measured quantitatively and used to automatically redirect both the laser delivery and eye tracking portions of the system independent of the laser positioning mechanism. The system operates without interfering with the particular treatment laser or the surgeon performing the eye treatment procedure.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

That which is claimed is:

1. A method of correcting vision by ablating corneal tissue comprising the steps of:

providing a laser beam for ablating corneal tissue;

the laser beam providing laser beam shots, each shot having a size, duration, and center point;

selecting an area of the cornea for ablation;

determining the size of the laser shots so that the shots are smaller than the the selected for ablation;

selecting a pattern and sequence for the placement of the laser beam shots on the selected area of the cornea to obtain the removal of a desired amount of corneal tissue;

placing the laser beam shots on the selected area of the cornea in the selected pattern and sequence;

the placed laser beam shots ablating corneal tissue;

subsequent shots in the pattern having their centers spaced at least one shot size apart;

the pattern and sequence selected such that no laser shots are fired at consecutive locations and such that no consecutive shots overlap; and, the pattern and sequence selected to allow a cloud of ablated corneal tissue particles to dissipate in one place before contacting that place again with another laser shot.

2. The method recited in claim 1, wherein the laser beam shot placing step comprises translating an incoming beam independently along each of two orthogonal translation axes to produce an output beam for ablating a desired corneal area.

3. The method recited in claim 2, wherein the translating step comprises maintaining a constant angle between the incoming beam and the output beam.

4. A method of correcting vision by ablating corneal tissue comprising the steps of:

providing a laser beam;

the laser beam providing laser beam shots, each shot having a size, duration, and center point;

selecting an area of the cornea for ablation;

selecting a pattern and sequence for the placement of the laser beam shots on the selected area of the cornea to obtain the removal of a desired amount of corneal tissue;

placing the laser beam shots on the selected area of the cornea in the selected pattern and sequence;

the laser shots ablating corneal tissue;

subsequent shots in the pattern having their centers spaced apart;

the pattern and sequence selected such that no laser shots are fired at consecutive locations and such that no consecutive shots overlap;

the pattern and sequence selected to allow a cloud of ablated corneal tissue particles to dissipate in one place before contacting that place again with another laser shot;

tracking movements of the selected area of the cornea; and, adjusting the placement of the shots on the selected area of the cornea to compensate for the tracked movements of the selected area.

5. The method recited in claim 4, wherein the laser beam shot placing step comprises translating an incoming beam independently along each of two orthogonal translation axes to produce an output beam for ablating a desired corneal area.

6. The method recited in claim 5, wherein the translating step comprises maintaining a constant angle between the incoming beam and the output beam.

7. A method of correcting vision by ablating corneal tissue comprising the steps of:

providing a laser beam;

the laser beam providing a laser beam shot, the shot having a size, duration, and center point;

selecting an area of the cornea;

the size of the laser shot less than the selected area of the cornea;

placing at least three shots on the selected area of the cornea in a predetermined pattern and sequence;

the laser shots ablating corneal tissue;

subsequent shots in the pattern having their centers spaced apart;

the pattern and sequence selected such that no laser shots are fired at consecutive locations and such that no consecutive shots overlap;

the distance and time between the center point and placement of the first laser shot and the center point and placement of the second laser shot being sufficient so that any plume of ablated material from the first laser shot will not substantially interfere with the second laser shot;

the distance and time between the center point and placement of the second laser shot and the center and placement of the third laser shot being sufficient so that any plume of ablated material from the second laser shot will not substantially interfere with the third laser shot; and, whereby the predetermined pattern and sequence of shot placement allows a cloud of ablated corneal tissue particles to dissipate in one place before contacting that place again with another laser shot.

8. The method recited in claim 7, wherein the laser beam shot placing step comprises translating an incoming beam independently along each of two orthogonal translation axes to produce an output beam for ablating a desired corneal area.

9. The method recited in claim 8, wherein the translating step comprises maintaining a constant angle between the incoming beam and the output beam.

10. A method of correcting vision by ablating corneal tissue comprising the steps of:

providing a laser beam;

the laser beam providing laser beam shot, the shot having a size, duration, and center point;

selecting an area of the cornea of an eye;

the size of the laser shot less than the area of the cornea selected for ablation;

placing at least three shots on the selected area of the cornea in a predetermined pattern and sequence;

the laser shots ablating corneal tissue;

subsequent shots in the pattern having their centers spaced apart;

the pattern and sequence selected such that no laser shots are fired at consecutive locations and such that no consecutive shots overlap;

the distance and time between the center point and placement of the first laser shot and the center point and placement of the second laser shot being sufficient so that any plume of ablated material from the first laser shot will not substantially interfere with the second laser shot;

the distance and time between the center point and placement of the second laser shot and the center and placement of the third laser shot being sufficient so that any plume of ablated material from the second laser shot will not substantially interfere with the third laser shot;

the pattern and sequence of shot placement selected so as to allow a cloud of ablated corneal tissue particles to dissipate in one place before contacting that place again with another laser shot;

tracking movements of the eye; and adjusting the placement of the shots on the selected area of the cornea to compensate for the tracked movements of the eye.

11. The method recited in claim 10, wherein the laser beam shot placing step comprises translating an incoming beam independently along each of two orthogonal translation axes to produce an output beam for ablating a desired corneal area.

12. The method recited in claim 11, wherein the translating step comprises maintaining a constant angle between the incoming beam and the output beam.

* * * * *

EX PARTE REEXAMINATION CERTIFICATE (6385th)

United States Patent
Frey et al.

(10) Number: US 6,626,896 C1
(45) Certificate Issued: *Aug. 19, 2008

(54) METHOD OF CORRECTING VISION

(75) Inventors: Rudolph W. Frey, Orlando, FL (US); James H. Burkhalter, Orlando, FL (US); Gary P. Gray, Orlando, FL (US); Neil Zepkin, Casselberry, FL (US); George Richard Downes, Jr., Orlando, FL (US); John E. McWhirter, Orlando, FL (US)

(73) Assignee: Alcon Universal Ltd., Hunenberg (CH)

Reexamination Request:
No. 90/007,291, Nov. 15, 2004

Reexamination Certificate for:
Patent No.: 6,626,896
Issued: Sep. 30, 2003
Appl. No.: 09/742,884
Filed: Dec. 21, 2000

( * ) Notice: This patent is subject to a terminal disclaimer.

Related U.S. Application Data

(63) Continuation of application No. 09/376,133, filed on Aug. 17, 1999, now Pat. No. 6,451,008, which is a continuation of application No. 08/232,615, filed on Apr. 25, 1994, now Pat. No. 5,980,513.

(51) Int. Cl.
*A61F 9/007* (2006.01)

(52) U.S. Cl. .................. 606/12; 606/5; 606/10; 606/13

(58) Field of Classification Search .............. 606/4, 606/5, 10–12; 351/208–210; 128/898
See application file for complete search history.

(56) References Cited

U.S. PATENT DOCUMENTS

| 5,520,679 A | 5/1996 | Lin |
| 6,090,100 A | 7/2000 | Hohla |
| 6,210,401 B1 * | 4/2001 | Lai .............. 606/12 |
| 6,706,036 B2 * | 3/2004 | Lai .............. 606/12 |

FOREIGN PATENT DOCUMENTS

| WO | WO 93/08877 | 5/1993 |
| WO | WO 94/07447 | 4/1994 |

* cited by examiner

*Primary Examiner*—Beverly M. Flanagan

(57) ABSTRACT

An opthalmic laser system includes a laser beam delivery system and an eye tracker responsive to movement of the eye operable with a laser beam delivery system for ablating corneal material of the eye through placement of laser beam shot on a selected area of the cornea of the eye. The shots are fired in a sequence and pattern such that no laser shots are fired at consecutive locations and no consecutive shots overlap. The pattern is moved in response to the movement of the eye.

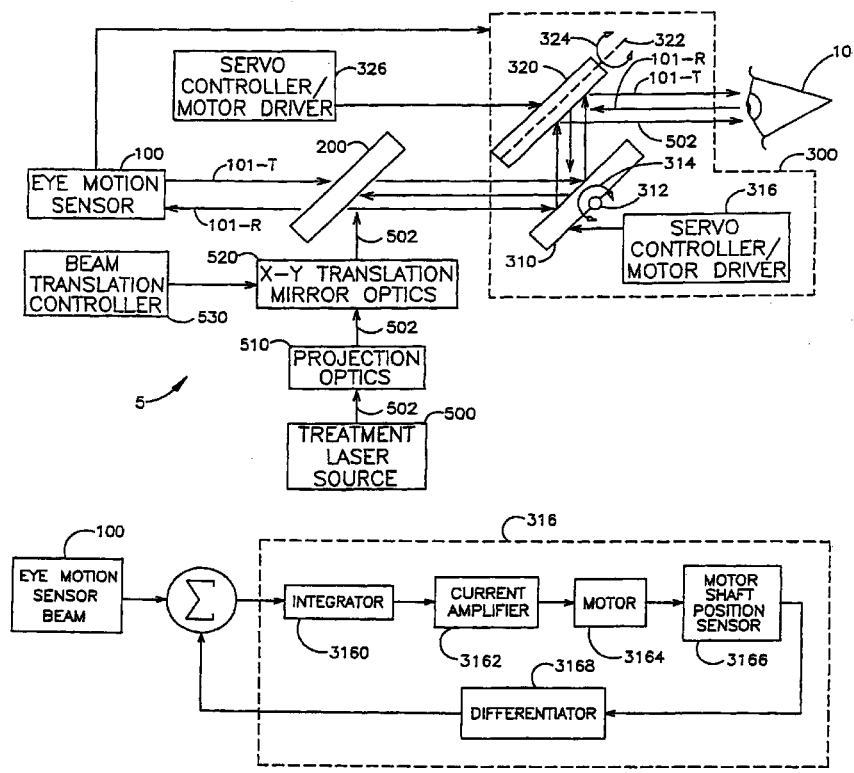

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3, 4, 6, 7, 9, 10 and 12 are determined to be patentable as amended.

Claims 2, 5, 8 and 11, dependent on an amended claim, are determined to be patentable.

1. A method of correcting vision by ablating corneal tissue comprising the steps of:
   providing [a] *an excimer* laser beam for ablating corneal tissue;
   the laser beam providing laser beam shots, each shot having a size, duration, and center point;
   selecting an area of the cornea for ablation;
   determining the size of the laser shots so that the shots are smaller than the [the] selected *area* for ablation;
   selecting a pattern and sequence for the placement of the laser beam shots on the selected area of the cornea to obtain the removal of a desired amount of corneal tissue;
   placing the laser beam shots on the selected area of the cornea in the selected pattern and sequence;
   the placed laser beam shots ablating corneal tissue;
   subsequent shots in the pattern having their centers spaced at least one shot size apart;
   the pattern and sequence *are* selected such that no *two consecutive* laser shots are fired at [consecutive] *adjacent* locations and such that no consecutive shots overlap; and,
   the pattern and sequence selected to allow a cloud of ablated corneal tissue particles to dissipate in one place before contacting that place again with another laser shot.

3. [The method recited in claim 2]*A method of correcting vision by ablating corneal tissue comprising the steps of:*
   *providing a laser beam for ablating corneal tissue;*
   *the laser beam providing laser beam shots, each shot having a size, duration and center point;*
   *selecting an area of the cornea for ablation;*
   *determining the size of the laser shots so that the shots are smaller than the selected area for ablation;*
   *selecting a pattern and sequence for placement of the laser beam shots on the selected area of the cornea to obtain the removal of a desired amount of corneal tissue;*
   *placing the laser beam shots on the selected area of the cornea in the selected pattern and sequence;*
   *the placed laser beam shots ablating corneal tissue;*
   *subsequent shots in the pattern having their centers spaced at least one shot size apart;*
   *the pattern and sequence are selected such that no two consecutive laser shots are fired at adjacent locations and such that no consecutive shots overlap; and*
   *the pattern and sequence selected to allow a cloud of ablated corneal tissue particles to dissipate in one place before contacting that place again with another laser shot,*
   wherein the laser beam shot placing step comprises translating an incoming beam independently along each of two orthogonal translation axes to produce an output beam for ablating a desired corneal area,
   wherein the translating step comprises maintaining a constant angle between the incoming beam and the output beam.

4. A method of correcting vision by ablating corneal tissue comprising the steps of:
   providing [a] *an excimer* laser beam;
   the laser beam providing laser beam shots, each shot having a size, duration, and center point;
   selecting an area of the cornea for ablation;
   selecting a pattern and sequence for placement of the laser beam shots on the selected area of the cornea to obtain the removal of a desired amount of corneal tissue;
   placing the laser beam shots on the selected area of the cornea in the selected pattern and sequence;
   the laser shots ablating corneal tissue;
   subsequent shots in the pattern having their centers spaced apart;
   the pattern and sequence selected such that no laser shots are fired at consecutive locations and such that no consecutive shots overlap;
   the pattern and sequence selected to allow a cloud of ablated corneal tissue particles to dissipate in one place before contacting that place again with another laser shot;
   tracking movements of the selected area of the cornea; and,
   adjusting the placement of the shots on the selected area of the cornea to compensate for the tracked movements of the selected area.

6. [The]*A* method [recited in claim 5] *of correcting vision by ablating corneal tissue comprising the steps of:*
   *providing a laser beam for ablating corneal tissue;*
   *the laser beam providing laser beam shots, each shot having a size, duration and center point;*
   *selecting an area of the cornea for ablation;*
   *determining the size of the laser shots so that the shots are smaller than the selected area for ablation;*
   *tracking movements of the selected area of the cornea; and,*
   *adjusting the placement of the shots on the selected area of the cornea to compensate for the tracked movements of the selected area;*
   *selecting a pattern and sequence for placement of the laser beam shots on the selected area of the cornea to obtain the removal of a desired amount of corneal tissue;*
   *placing the laser beam shots on the selected area of the cornea in the selected pattern and sequence;*
   *the placed laser beam shots ablating corneal tissue;*
   *subsequent shots in the pattern having their centers spaced at least one shot size apart;*
   *the pattern and sequence are selected such that no two consecutive laser shots are fired at adjacent locations and such that no consecutive shots overlap; and* the pattern and sequence selected to allow a cloud of ablated corneal tissue particles to dissipate in one place before contacting that place again with another laser shot, wherein the laser beam shot placing step comprises translating an incoming beam independently along each of two orthogonal translation axes to produce an output beam for ablating a desired corneal area, and, wherein the translating step comprises maintaining a constant angle between the incoming beam and the output beam.

7. A method of correcting vision by ablating corneal tissue comprising the steps of:

providing [a] *an excimer* laser beam;

the laser beam providing a laser beam shot, the shot having a size, duration, and center point;

selecting an area of the cornea;

the size of the laser shot less than the selected area of the cornea;

placing at least three shots on the selected area of the cornea in a predetermined pattern and sequence;

the laser shots ablating corneal tissue;

subsequent shots in the pattern having their centers spaced apart;

the pattern and sequence selected *for application of said three laser shots* such that no *consecutive* laser shots are fired at [consecutive] *adjacent* locations and such that no consecutive shots overlap;

the distance and time between the center point and placement of the first laser shot and the center point and placement of the second laser shot being sufficient so that any plume of ablated material from the first laser shot will not substantially interfere with the second laser shot;

the distance and time between the center point and placement of the second laser shot and the center and placement of the third laser shot being sufficient so that any plume of ablated material from the second laser shot will not substantially interfere with the third laser shot; and whereby the predetermined pattern and sequence of shot placement allows a cloud of ablated corneal tissue particles to dissipate in one place before contacting that place again with another laser shot.

9. [The method recited in claim 8] *A method of correcting vision by ablating corneal tissue comprising the steps of:*

*providing a laser beam;*

*the laser beam providing a laser beam shot, the shot having a size, duration, and center point;*

*selecting an area of the cornea;*

*the size of the laser shot being less than the selected area of the cornea;*

*placing at least three shots on the selected area of the cornea in a predetermined pattern and sequence;*

*the laser shots ablating corneal tissue;*

*subsequent shots in the pattern having their centers spaced apart;*

*the pattern and sequence selected for application of said three laser shots such that no consecutive laser shots are fired at adjacent locations and such that no consecutive shots overlap;*

*the distance and time between the center point and placement of the first laser shot and the center point and placement of the second laser shot being sufficient so that any plume of ablated material from the first laser shot will not substantially interfere with the second laser shot;*

*the distance and time between the center point and placement of the second laser shot and the center and placement of the third laser shot being sufficient so that any plume of ablated material from the second laser shot will not substantially interfere with the third laser shot; and*

*whereby the predetermined pattern and sequence of shot placement allows a cloud of ablated corneal tissue particles to dissipate in one place before contacting that place again with another laser shot, and*

*wherein the laser beam shot placing step comprises translating an incoming beam independently along each of two orthogonal translation axes to produce an output beam for ablating a desired corneal area, and, wherein the translating step comprises maintaining a constant angle between the incoming beam and the output beam.*

10. A method of correcting vision by ablating corneal tissue comprising the steps of:

providing [a] *an excimer* laser beam;

the laser beam providing laser beam shot, the shot having a size, duration, and center point;

selecting an area of the cornea of an eye;

the size of the laser shot *being* less than the area of the cornea selected for ablation;

placing at least three shots on the selected area of the cornea in a predetermined pattern and sequence;

the laser shots ablating corneal tissue;

subsequent shots in the pattern having their centers spaced apart;

the pattern and sequence selected such that no *consecutive* laser shots are fired at [consecutive] *adjacent* locations and such that no consecutive shots overlap;

the distance and time between the center point and placement of the first laser shot and the center point and placement of the second laser shot being sufficient so that any plume of ablated material from the first laser shot will not substantially interfere with the second laser shot;

the distance and time between the center point and placement of the second laser shot and the center and placement of the third laser shot being sufficient so that any plume of ablated material from the second laser shot will not substantially interfere with the third laser shot;

the pattern and sequence of shot placement selected so as to allow a cloud of ablated corneal tissue particles to dissipate in one place before contacting that place again with another laser shot;

tracking movements of the eye; and adjusting the placement of the shots on the selected area of the cornea to compensate for the tracked movements of the eye.

12. [The method recited in claim 11] *A method of correcting vision by ablating corneal tissue comprising the steps of:*

*providing a laser beam;*

*the laser beam providing laser beam shot, the shot having a size, duration, and center point;*

*selecting an area of the cornea of an eye;*

*the size of the laser shot being less than the area of the cornea selected for ablation;*

*placing at least three shots on the selected area of the cornea in a predetermined pattern and sequence;*

*the laser shots ablating corneal tissue;*

*subsequent shots in the pattern having their centers spaced apart;*

*the pattern and sequence selected such that no consecutive laser shots are fired at adjacent locations and such that no consecutive shots overlap;*

*the distance and time between the center point and placement of the first laser shot and the center point and placement of the second laser shot being sufficient so that any plume of ablated material from the first laser shot will not substantially interfere with the second laser shot;*

*the distance and time between the center point and placement of the second laser shot and the center and placement of the third laser shot being sufficient so that any plume of ablated material from the second laser shot will not substantially interfere with the third laser shot;*

*the pattern and sequence of shot placement being selected so as to allow a cloud of ablated corneal tissue particles to dissipate in one place before contacting that place again with another laser shot;*

*tracking movements of the eye; and*

*adjusting the placement of the shots on the selected area of the cornea to compensate for the tracked movements of the eye, and*

*wherein the laser beam shot placing step comprises translating an incoming beam independently along each of two orthogonal translation axes to produce an output beam for ablating a desired corneal area and, wherein the translating step comprises maintaining a constant angle between the incoming beam and the output beam.*

\* \* \* \* \*